US008740928B2

(12) United States Patent
Göbel

(10) Patent No.: US 8,740,928 B2
(45) Date of Patent: Jun. 3, 2014

(54) GASTRIC TUBE

(75) Inventor: Fred G. Göbel, Wihelmsfeld (DE)

(73) Assignee: Microcuff GmbH, Weinheim (DE)

( * ) Notice: Subject to any disclaimer, the term of this patent is extended or adjusted under 35 U.S.C. 154(b) by 1042 days.

(21) Appl. No.: 12/280,239

(22) PCT Filed: Jan. 9, 2007

(86) PCT No.: PCT/EP2007/000128

§ 371 (c)(1),
(2), (4) Date: Nov. 14, 2008

(87) PCT Pub. No.: WO2007/096022

PCT Pub. Date: Aug. 30, 2007

(65) Prior Publication Data

US 2009/0222030 A1 Sep. 3, 2009

(30) Foreign Application Priority Data

Feb. 22, 2006 (DE) ..................... 20 2006 002 832 U

(51) Int. Cl.
*A61B 17/08* (2006.01)

(52) U.S. Cl.
USPC .......................................................... 606/196

(58) Field of Classification Search
USPC ......... 606/153, 154, 155, 156, 184, 191, 192, 606/193, 194, 195, 196, 197, 198, 199; 604/96.01, 103.09, 104, 106, 105, 107
See application file for complete search history.

(56) References Cited

U.S. PATENT DOCUMENTS 3,480,017 A * 11/1969 Shute ............................ 606/193
3,850,176 A * 11/1974 Gottschalk .................... 606/196
4,141,364 A * 2/1979 Schultze ................. 128/207.15
4,276,874 A * 7/1981 Wolvek et al. .................. 600/18
4,534,349 A * 8/1985 Barrows ........................ 606/152
4,705,039 A * 11/1987 Sakaguchi et al. ............ 606/154

(Continued)

FOREIGN PATENT DOCUMENTS

WO WO 98/13090 A 4/1998
WO WO 03/045485 A 6/2003

OTHER PUBLICATIONS

Merriam-Webster definition of "lumen" as accessed on Jul. 11, 2013; http://www.merriam-webster.com/dictionary/lumen.*
International Search Report, issued Nov. 30, 2007.

*Primary Examiner* — Tuan V Nguyen
*Assistant Examiner* — Jonathan W Miles
(74) *Attorney, Agent, or Firm* — Dority & Manning, P.A.

(57) ABSTRACT

With the invention, a gastric tube with an inflatable stopper and a supply cannula that can be introduced into the oesophagus and on which a lumen is superposed in the region of the inflatable stopper, which is connected to the interior of the inflatable stopper and permits a rapid volume equalization between different regions of the inflatable stopper, is to be improved in that the lumen which is located between the supply cannula and the inflatable stopper and connected to the interior of the inflatable stopper, can be produced in a technically simple manner and at the same time provides sufficient volume equalization between partial volumes of the inflatable stopper. This object is achieved by a gastric tube with an inflatable stopper in which a separate molding body is mounted on the supply cannula which determines the shape of the lumen.

22 Claims, 3 Drawing Sheets

(56) References Cited

U.S. PATENT DOCUMENTS

Figure 3:
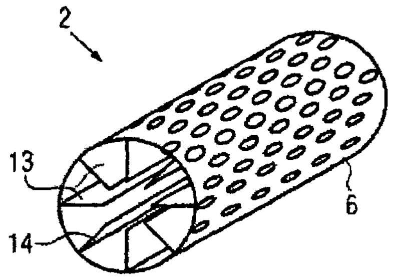

| | | | | | |
|---|---|---|---|---|---|
| 4,848,367 | A | * | 7/1989 | Avant et al. | 128/898 |
| 5,030,227 | A | * | 7/1991 | Rosenbluth et al. | 606/192 |
| 5,176,144 | A | * | 1/1993 | Yoshikoshi et al. | 600/505 |
| 5,195,971 | A | * | 3/1993 | Sirhan | 604/103.1 |
| 5,257,974 | A | * | 11/1993 | Cox | 604/103.05 |
| 5,275,622 | A | * | 1/1994 | Lazarus et al. | 623/1.11 |
| 5,344,402 | A | * | 9/1994 | Crocker | 604/103.01 |
| 5,378,237 | A | * | 1/1995 | Boussignac et al. | 604/103.01 |
| 5,425,709 | A | * | 6/1995 | Gambale | 604/103.05 |
| 5,443,477 | A | * | 8/1995 | Marin et al. | 606/198 |
| 5,505,699 | A | * | 4/1996 | Forman et al. | 604/103.09 |
| 5,507,766 | A | * | 4/1996 | Kugo et al. | 606/194 |
| 5,562,728 | A | * | 10/1996 | Lazarus et al. | 623/1.14 |
| 5,653,689 | A | * | 8/1997 | Buelna et al. | 604/103.09 |
| 5,653,760 | A | * | 8/1997 | Saffran | 623/11.11 |
| 5,882,347 | A | * | 3/1999 | Mouris-Laan et al. | 604/524 |
| 5,891,090 | A | * | 4/1999 | Thornton | 604/103.09 |
| 6,017,352 | A | * | 1/2000 | Nash et al. | 606/153 |
| 6,315,757 | B1 | * | 11/2001 | Chee et al. | 604/103.09 |
| 6,500,147 | B2 | * | 12/2002 | Omaleki et al. | 604/103.09 |
| 6,551,272 | B2 | * | 4/2003 | Gobel | 604/96.01 |
| 7,794,425 | B2 | * | 9/2010 | Gobel | 604/101.05 |
| 2004/0153116 | A1 | * | 8/2004 | Nobles et al. | 606/193 |
| 2006/0030814 | A1 | * | 2/2006 | Valencia et al. | 604/93.01 |
| 2007/0106216 | A1 | * | 5/2007 | Noddin | 604/103.09 |
| 2007/0203515 | A1 | * | 8/2007 | Heuser et al. | 606/184 |
| 2008/0119922 | A1 | * | 5/2008 | Alkhatib | 623/1.11 |

* cited by examiner

FIG. 1
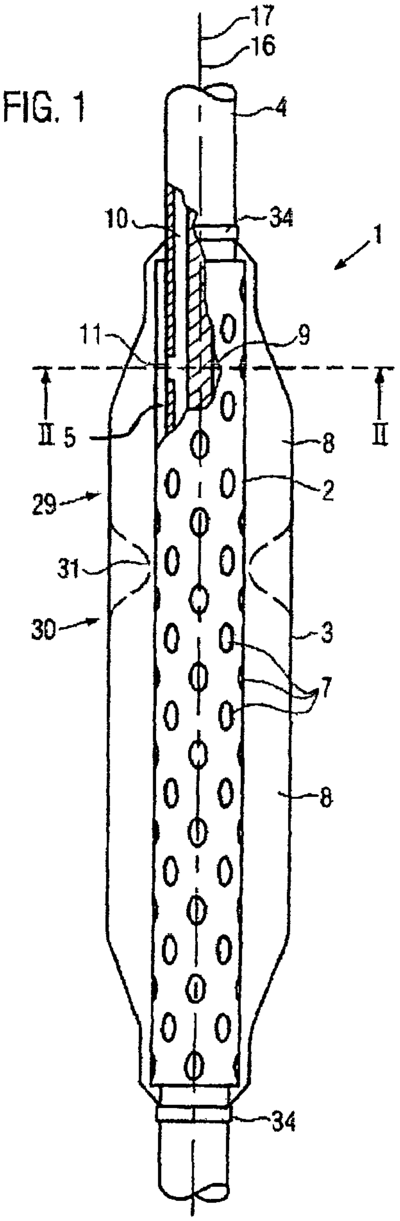
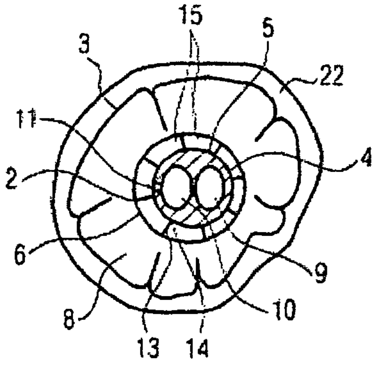
FIG. 2

GASTRIC TUBE

The invention relates to a gastric tube.

In a gastric tube of this type known from WO 98/13090, a lumen is superposed on the supply cannula in the region of the inflatable stopper, said lumen ensuring a rapid volume equalization between partial regions or partial volumes of the inflatable stopper. The lumen is arranged such that a channel is formed between the lumen and the supply cannula which is connected to the interior of the inflatable stopper via a plurality of openings which is arranged on the lumen. The interior of the inflatable stopper is connected to means for generating the pressure in the inflatable stopper via the channel formed between the supply cannula and the lumen. In the process, the lumen is maintained by web-like structures or spacers between an outer and an inner wall of the tube or the supply cannula of the gastric tube. Such a gastric tube is therefore much more complicated to manufacture than e.g. current gastric tubes without lumen.

The object underlying the invention is to improve a gastric tube of the type mentioned in the beginning such that the lumen, which is located between the supply cannula and the inflatable stopper and is connected to the interior of the inflatable stopper, can be produced in a technically simple manner and at the same time provides sufficient volume equalization between partial volumes of the inflatable stopper.

In some embodiments, this object is achieved by a gastric tube having a separate molding body mounted on a supply cannula, where the separate molding body determines the shape of a lumen The separate molding body can be produced in a technically simple manner as it can be prefabricated as individual part. During the assembly of the gastric tube, it is mounted or attached on the supply cannula as a module. Thereby, the assembly of the gastric tube is facilitated as the number of individual processing steps required to prepare the lumen can be reduced. This includes a potential for improving productivity as concerns time as well as costs for the manufacture of the gastric tube. With the mounting of the molding body onto the supply cannula, the shape of the lumen, which provides sufficiently rapid volume exchange between partial regions of the inflatable stopper, is at the same time determined.

In an advantageous embodiment of the invention, the molding body can have a tubular structure the inner contour of which approximately corresponds to the outer contour of the supply cannula. The tubular structure permits to mount the molding body approximately concentrically onto the supply cannula. This facilitates assembly.

Favorably, the molding body can comprise at least one opening which extends approximately into the longitudinal direction of the molding body over at least 50 to 60%, advantageously up to 70%, and in particular up to 80% of the overall length of the molding body and connects the lumen to the interior of the inflatable stopper. This opening ensures sufficient volume equalization between various partial regions of the inflatable stopper.

Advantageously, the opening can extend over the complete length of the molding body. The opening ensures good volume equalization between partial regions of the inflatable stopper and can be moreover produced in a technically simple manner.

In a favorable embodiment of the invention, the molding body can comprise, in the cross-section, several wall elements extending radially, which comprise a surface at their extreme ends which extends approximately transversely to the respective wall element. The surfaces extending approximately transversely to the wall elements offer a good contact surface for the inflatable stopper. The wall elements extending radially with respect to them ensure a sufficient distance of the surfaces to the supply cannula and thus provide a sufficiently large lumen for good volume equalization. The size and the number of the individual partial lumens can be determined depending on the number of wall elements.

In a further embodiment of the invention, at least one of the wall elements can have an approximately T-shaped profile. This profile can be easily produced and offers a sufficiently large lumen as well as a good contact surface for the inflatable stopper.

Advantageously, at least one of the wall elements can have an approximately L-shaped profile. This profile can also be produced in a technically simple manner and ensures a lumen as well as a contact surface which permits a rapid volume exchange between partial regions of the inflatable stopper.

In a variant of the invention, the cross-section of the molding body can comprise several wall regions which are supported at the supply cannula of the tube and define, together with the same, at least one partial region of the lumen. These wall regions, which project inwards similar to a finger, can form a passage by their frontal ends the dimensions of which approximately correspond to those of the supply cannula. Thus, the molding body can be easily mounted onto the supply cannula.

Advantageously, the wall regions can extend approximately like a star into the interior of the molding body. This shape ensures approximately uniformly distributed wall regions. This offers a good support and holding function for the molding body.

In one variant of the invention, the molding body can comprise at least one spirally shaped coil. The coil can be produced in a technically simple manner and can be easily mounted onto the supply channel. Moreover, it offers a sufficiently large lumen for a good volume exchange between the individual windings of the coil.

In a favorable embodiment of the invention, an element approximately embodied like a hose can be arranged on the coil, said element comprising several openings distributed across its surface. Thereby, the contact surface for the inflatable stopper is enlarged.

In a further embodiment of the invention, the element embodied like a hose can have a netlike design. This netlike structure can be produced in a technically simple manner and can be premounted on the coil. Thus, assembly is facilitated.

In an advantageous embodiment of the invention, the molding body can comprise one or several layers of a netlike structure. By the individual openings in the net structure or their overlapping, a sufficiently large lumen is defined which permits good volume exchange between partial regions of the inflatable stopper.

Favorably, the lumen can be connected, in the region of the axial frontal side of the molding body, to a supply channel via which the inflatable stopper can be filled with a fluid. This can be technically easily produced and constructively simplifies the gastric tube as the inflatable stopper can thus be filled directly via the lumen connected thereto.

Advantageously, the molding body can consist of PVC, PUR, mixtures of PVC and PUR, mixtures of PUR and polyamides and/or silicone. These materials ensure good compatibility. They can be easily deformed and thus reduce the risk of injuries when the tube is being inserted, and they nevertheless are sufficiently stable to maintain the lumen.

In a favorable embodiment, the molding body can be produced by extruding. This manufacturing process permits to manufacture the molding body in a technically relatively simple manner easily and within a short time.

In a variant of the invention, the molding body can be fixed on the supply cannula with frictional engagement. Thereby, the molding body is fixed in its position relative to the supply cannula.

In another embodiment of the invention, the molding body can be fixed on the supply cannula by means of an interference fit. This ensures an axial and/or radial fixing of the molding body on the supply cannula of the gastric tube.

Favorably, the molding body can be fixed on the supply cannula by means of adhesion. This technically simple method, e.g. gluing, ensures sufficient fixing of the molding body.

In another embodiment of the invention, the molding body can be fixed on the supply cannula with a material connection. This ensures a qualitatively high-grade connection between the molding body and the supply cannula.

Advantageously, the molding body can comprise, at least in sections, a connection to the supply cannula generated by means of a solvent. The solubilization of the molding body and/or of the supply cannula at least in sections ensures a good connection of the two components.

In a favorable embodiment of the invention, the outside diameter of the molding body can approximately be between 7 to 12 mm, in particular between 6 to 8 mm. These dimensions ensure a good volume exchange between partial regions of the inflatable stopper.

Advantageously, the length of the molding body can be approximately between 6 to 12 cm, in particular between 6 to 9 cm. These linear dimensions proved to be advantageous. They offer a sufficiently large contact surface for the inflatable stopper. At the same time, a sufficient volume exchange between all partial regions of the inflatable stopper is permitted.

In a further embodiment of the invention, the gastric tube can be provided with at least one radiopaque marker. The marker, e.g. a metal ring, facilitates the placing of the tube in the patient and permits a good reference to orientating structures, such as e.g. the diaphragm and/or the hyoid bone, in the radiograph of the thorax.

Figure 4:
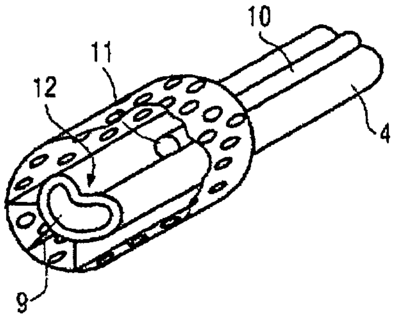
Figure 5:
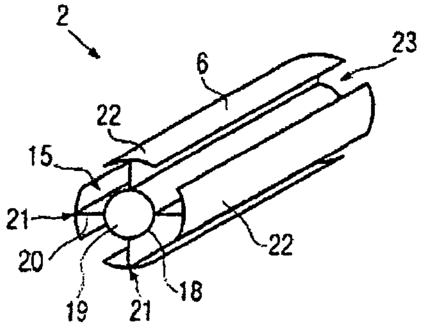
Figure 6:
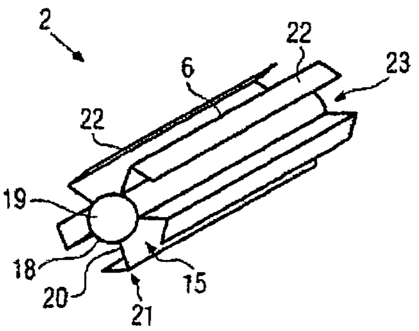
Figure 7:
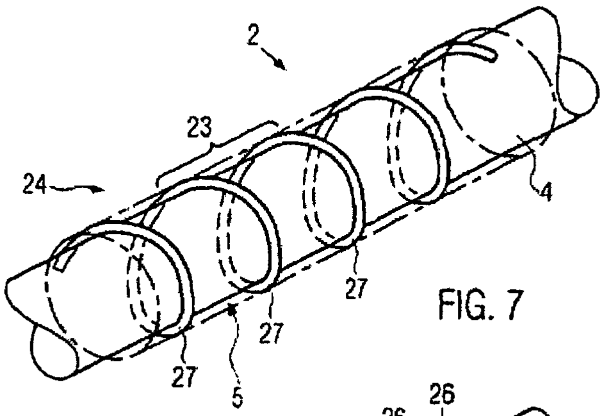
Figure 8:
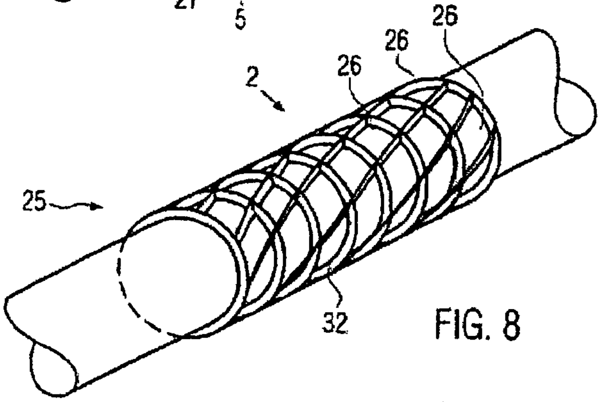

In the following, embodiments of the invention are described with reference to the following drawings. In the drawings:

FIG. 1 shows a detail in the region of the inflatable stopper of a gastric tube according to the invention with a first embodiment of a molding body according to the invention, FIG. 2 shows a cross-section through the gastric tube of FIG. 1 according to the invention, FIG. 3 shows a perspective view of the inventive molding body of FIGS. 1 and 2 according to a first embodiment, FIG. 4 shows a perspective view of the supply cannula, FIG. 5 shows a perspective view of an inventive molding body according to a second embodiment, FIG. 6 shows a perspective view of an inventive molding body according to a third embodiment, FIG. 7 shows a perspective view of an inventive molding body according to a fourth embodiment, and FIG. 8 shows a perspective view of an inventive molding body according to a fifth embodiment.

FIG. 1 shows the principal structure of a gastric tube 1 according to the invention. In the region of the inflatable stopper 3, a molding body 2 is superposed on the supply cannula 4, said molding body including a lumen 5 inside. The lumen 5 is represented in FIG. 2 which represents the section II-II through the gastric tube of FIG. 1. In this embodiment, the lumen 5 is located between the supply cannula 4 and the surface 6 of the molding body 2. As can be seen in FIG. 1, the molding body 2 is provided with several openings 7 which are distributed across the complete surface 6 of the molding body 2. Via the openings 7, the lumen is connected to the interior 8 of the inflatable stopper 3. That means, the openings 7 permit a volume or fluid exchange between the lumen 5 and the interior 8 of the inflatable stopper 3.

The number and shape of the opening 7 can vary depending on the application. Apart from the approximately round or oval openings 7 shown here, e.g. oblong openings are also possible. The shape or the contour of the openings 7 can be round or oval, or else three-, four- or polygonal openings. Moreover, the openings do not have to be, as shown here, distributed approximately uniformly across the surface 6 of the molding body 2. As an alternative, a non-uniform distribution of the openings 7 is possible. The important thing is that the shape and arrangement of the openings permit sufficient volume exchange between two partial regions 29 and 30 of the inflatable stopper 3. The number of the openings can vary from one to an arbitrary number of individual openings, e.g. 100 or 1000 openings. The number is only limited by the size of the surface 6 of the molding body 2 and the shape of the openings.

The outside diameter of the supply cannula 4 is advantageously between 3 to 6 mm, and in particular between 4 to 5 mm. In its interior, there is provided a channel 9, which provides the patient with a nutrient solution, as well as a supply channel 10 via which the inflatable stopper 3 can be filled with a fluid, e.g. water. Depending on the application, various fluids, e.g. gas or gas mixtures, such as air, or else viscous liquids, can be employed. The diameter of the inflatable stopper 3 in its completely unfolded state is approx. 20 to 50 mm. Particularly favorable is a diameter of 30 to 40 mm. The supply channel 10 for the fluid extends in this embodiment at least in sections into the molding body 2 and has a connection opening 11 extending radially to the molding body 2 which connects the supply channel 10 with the lumen 5.

In other embodiments of the gastric tube 1 according to the invention, the supply channel 10 can also extend externally along the supply cannula 4. For example, it can be at least partially arranged in an indentation 12 extending along the supply cannula 4, as represented in FIG. 4. The connection opening 11 of the supply channel 10 does not necessarily have to extend radially, but it can also end in the region of the axial front face of the molding body 2, thus extending axially to the molding body 2.

FIG. 3 shows the molding body 2 according to the invention of the first embodiment in an enlarged representation. The molding body 2 has an overall length of approximately 6 to 9 cm and here has an approximately cylindrical outer contour. Starting from the cylindrical surface 6, several wall regions 13 extend radially into the interior of the molding body 2. The free, frontal ends 14 of the wall regions 13 define a diameter which approximately corresponds to the outside diameter of the supply cannula 4. In the inserted state, that means, when the molding body 2 is located on the supply cannula 4, the frontal ends 14 of the wall regions 13 support themselves on the supply cannula 4, as can be seen in FIG. 2. Together with the supply cannula 4, they divide the lumen 5 in the interior of the molding body 2 into individual partial lumens 15. One individual partial lumen 15 is limited each by two wall regions 13, the partial region of the molding body surface 6 arranged between the two wall regions 13, and the partial region of the supply cannula surface, which is located between the contact surfaces of the frontal ends 14 of the wall regions 13. In this embodiment, the molding body 2 has eight wall regions which all project like fingers into the molding body approximately to the same extent. In other embodiments of the invention, the number of wall regions, however, can vary arbitrarily and thus have an influence on the shape of the lumen 5 or the individual partial lumens 15, respectively. The depth to which the wall regions 13 project into the interior of the molding body 2 can also vary and thus determine the position of the molding body 2 relative to the supply cannula 4. That means, the molding body 2 does not necessarily have to sit approximately concentrically on the supply cannula 4, as shown here. Depending on the application, the longitudinal axis 16 of the molding body 2 can also be offset with respect to the longitudinal axis 17 of the supply cannula 4.

FIGS. 5 to 8*b* show further embodiments of molding bodies according to the invention in a perspective view.

FIGS. 5 and 6 show a molding body 2 according to the invention according to a second and a third embodiment. The reference numerals used in FIGS. 1 to 4 designate the same parts as in FIGS. 5 and 6. The molding bodies 2 comprise a central, approximately tubular structure 18 with an approximately circular cross-section. The shape of the inner surface area 19 approximately corresponds to the shape of the surface of the supply cannula 4. Starting from the central, tubular structure 18, several wall elements 20 extend radially outside. At the outermost end 21 opposite the central tubular structure 18 of each wall element 20, a surface 22 is provided which extends approximately transversely to the wall element 20.

In FIG. 5, the molding body 2 has four approximately crosswise arranged wall elements 20. The wall elements 20 form an approximately T-shaped profile in the cross-section together with the corresponding surfaces 22. The molding body 2 in FIG. 6 comprises five wall elements 20 which are arranged approximately like a star around the tubular structure 18. The wall elements 20, together with their respective cross-surfaces 22, result in an approximately L-shaped profile in the cross-section.

The T- or L-profiles of the molding bodies 2 of FIGS. 5 and 6 are spaced apart or dimensioned such that the cross surfaces 22 of two adjacent T- or L-profiles are spaced apart. That means that two of the cross surfaces 22 at a time define an opening 23 or a gap which extends longitudinally of the molding body 2, said cross surfaces 22 forming the surface 6 of the molding body 2. In these embodiments, the lumen 5 which is located here between the cross surfaces 22 and the tubular structure 18, is divided into individual partial lumens 15 by the T- or L-profiles. The shape of one individual partial lumen 15 is here determined by two adjacent T- or L-profiles at a time and the part of the surface of the tubular structure 18 enclosed by the same.

The number of wall elements 20 may be varied depending on the application. If it is varied, the shape and number of the partial lumens 15 and the openings 23 in the surface 6 of the molding body 2 also change. In other embodiments of the invention, the wall elements 20 can be arranged non-uniformly around the tubular structure 18, in contrast to the ones shown here. The cross surfaces 22 at the ends 21 of the wall elements 20 can also be omitted. In this case, the surface 6 of the molding body 2 is determined by the ends 21 of the wall elements 20. The number of wall elements 22 can be correspondingly increased and be e.g. between 5 to 15 wall elements.

FIG. 7 shows a further embodiment of the molding body 2 according to the invention. Here, the molding body 2 has a spiral shape and is embodied as a coil 24. The inside diameter of the coil 24 approximately corresponds to the outside diameter of the supply cannula 4. The lumen in this embodiment also has a spiral shape. In the inserted state, that means, when the molding body 2 is located on the supply cannula 4 here represented schematically, the windings 27 of the coil 24 define an opening 33 which winds spirally around the supply cannula 4 between the individual windings 27 of the coil 24 and accommodates the lumen 5. The material thickness of the coil 24 thereby determines the height of the lumen 5. The material cross-section here is approximately round. Alternatively, however, it can also have an oval or angular shape.

In a further embodiment, the lumen can also be defined by several, e.g. two coils, which are approximately concentrically shifted one upon the other. The two coils can comprise the same as well as different pitches. Moreover, the coils can be mounted on one another in opposite directions. In this case, the lumen 5 is defined by the space between the individual windings of the respective coil or the overlapping of these spaces.

A hose-like or tubular structure which is provided with openings and indicated in FIG. 7 by a dot-dash line can be mounted on the simple coil as well as on coils arranged one within the other. The outer shape of such a molding body would then be similar to the molding body shown in FIG. 1.

The above-described first to third embodiments of the molding body 2 according to the invention can also be embodied screw-like, twisted and thus as a coil.

FIG. 8 shows a fifth embodiment of the molding body 2 according to the invention. It has a tubular or hose-like shape and comprises a netlike structure 25. The inside diameter 2 of the molding body 2 approximately corresponds to the outside diameter of the supply cannula 4. Here, the lumen 5 is situated in the meshes or openings 26 of the netlike structure 25, which are at least partially connected to each other and thus permit a volume exchange between individual openings 26 of the netlike structure 25.

Figure 8B:
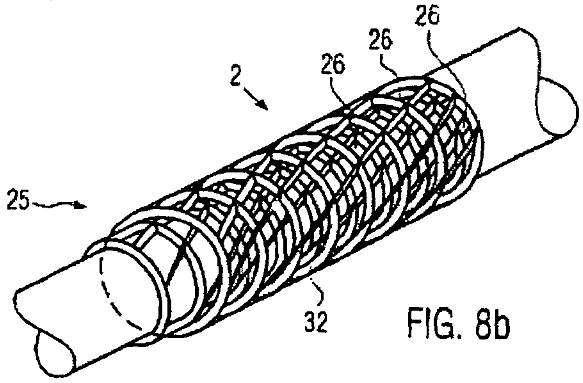

In a further embodiment of the invention, the molding body 2 can also comprise several layers of the netlike structure 25, as represented in FIG. 8*b*. These are then approximately concentrically arranged one within the other, wherein the inside diameter of the innermost layer approximately corresponds to the outside diameter of the supply cannula 4. The lumen 5 is determined here by the holes 26 of the netlike structure 25 which overlap at least partially. That means, the overlapping holes 26 of the individual layers of the netlike structure 25 form channels or individual partial lumens 15. In the inserted state of the molding body 2, that means when the same is located on the supply cannula 4, at least a portion of the partial lumens 15 extend at least in sections along the supply cannula 4 and thus permits a volume exchange between individual partial regions of the inflatable stopper 3.

The dimensions of the various embodiments of the molding body 2 described herein can vary depending on the application. In practice, however, an approximate length of 6 to 12 cm, and in particular a length of 6 to 9 cm of the molding body 2, has proved to be advantageous. The outside diameter also depends on the application, but also on the dimensions of the supply cannula 4 and the inflatable stopper 3, and is advantageously in a range of between 7 to 10 mm, in particular between 6 to 8 mm. In special applications, the dimensions of the molding body 2 can, however, differ from the ones mentioned above.

The molding body 2 described in the embodiments 1 to 5 is preferably made of plastics and fabricated by extruding. Alternatively, the molding body can also be manufactured by molding or injection molding. As materials for the molding body 2, in principle materials are possible which can be deformed in a body friendly manner, that is, which prevent injuries of the patient during insertion and long term recumbency of the tube, and which, however, have sufficient rigidity so as to ensure a non-collapsible shifting volume with a peristaltic passing over the molding body 2. Advantageous materials are e.g. PVC, PUR, mixtures of PVC and PUR, mixtures of PUR and polyamides as well as silicones.

For better localization, the gastric tube can be equipped with radiopaque markers, such as metal rings 34 or the like, as represented in FIG. 1. These can be provided at the molding body 2, the supply cannula 4 and/or around the inflatable stopper 3.

Below, the function of the embodiments represented in the Figures is illustrated.

For the assembly of the gastric tube 1 according to the invention, the molding body 2 is mounted onto the supply cannula 4, e.g. by shifting it on. As the inner diameter of the respective molding body 2 approximately corresponds to the outer diameter of the supply cannula 4 or is minimally smaller than the same, a slight interference fit is formed during the assembly of the molding body 2 on the supply cannula 4. The static friction resulting therefrom fixes the molding body 2 radially and axially on the supply cannula 4.

The molding body 2 can also be fixed to the supply cannula 4 by means of adhesion, e.g. by applying an adhesive in at least one partial region of the contact surface of the molding body 2 with the supply cannula 4.

Alternatively, the molding body can also be fixed by means of a material connection, by treating e.g. at least one partial region of the contact surface between the molding body 2 and the supply cannula 4 with a solvent.

In principle, any arbitrary combination of the above mentioned attachment possibilities is possible to fix the molding body 2 on the supply cannula 4.

In the molding body 2 shown in FIGS. 1 to 3, the inner or inside diameter of the molding body as well as the contact surface of the molding body 2 with the supply cannula 4 are formed by the frontal ends 14 of the wall elements 13. These abut against the surface of the supply cannula 4 during the assembly of the molding body 2 and thus divide the lumen 5 in the interior of the molding body 2 into individual partial lumens 15, as represented in FIG. 2.

In the embodiments of the molding body 2 represented in FIGS. 5 and 6, the inside diameter of the molding body as well as the contact surface of the molding body 2 with the supply cannula 4 are formed by the tubular structure 18.

In the coil 24, the fourth embodiment of the molding body 2 shown in FIG. 7, the inside diameter of the molding body 2 is determined by the inside diameter of the coil 24. The contact surface of the molding body 2 with the supply cannula 4 here corresponds to the also spirally extending contact line or surface of the individual windings 27 of the coil 24. Its form as line or surface depends on the material cross-section of the coil.

In the fifth embodiment of the molding body 2 represented in FIG. 8, the netlike structure 25, the inside diameter of the molding body 2 and the contact surface between the molding body 2 and the supply cannula 4 is determined by the individual webs 32 of the netlike structure 35.

The readily mounted gastric tube is employed e.g. for coma patients who cannot provide themselves with food anymore. For this purpose, the gastric tube 1 according to the invention or the supply cannula 4 of the gastric tube 1 is inserted into the gullet, i.e. oesophagus, of the patient. In doing so, the region of the gastric tube which is provided with the inflatable stopper 3 is placed above the stomach entry in the gullet. The advantageous length of the molding body 2 of approx. 6 to 9 mm ensures a good placing in the segment between the upper and the lower constrictor of the gullet. The radiopaque markers 34 permit to check the correct position of the tube by taking an X-ray. Via the supply channel 10, the inflatable stopper 3 is filled with a fluid, e.g. water. In doing so, the fluid flows through the connection opening 11 of the supply channel 10 into the lumen 5 of the molding body 2. Through the openings 7, 23, 26, 33 of the molding body 2, the fluid reaches the interior 8 of the inflatable stopper 3. By filling in the fluid, the inflatable stopper 3 expands until it is nearly completely lying against the wall of the gullet 28, as can be seen in FIG. 2. This permits to largely seal the gullet 28 against liquids or solids, which have the tendency of ascending from the stomach region towards the throat, and to thus keep the trachea free from disturbing influences.

Swallowing movements of the patient provided with the gastric tube according to the invention result in muscle contractions along the gullet. These cause one or often several annular contractions of the gullet which start in the voice box region and move towards the stomach, thus along the gullet.

To illustrate the functioning of the molding body 2, the movement of a single annular contraction is looked at below. In the region of the inflatable stopper, the annular contraction leads to a partial reduction of the outside diameter of the inflatable stopper, that means to a local constriction 31 of the inflatable stopper 3 which is represented in FIG. 1 by a dashed line. This divides the inflatable stopper into two partial regions 29 and 30. While the constriction 31 moves along the inflatable stopper 3, the dimensions of the individual partial regions 29, 30 change. Thereby, however, the fluid volume which can be accommodated in the respective partial regions 29, 30 of the inflatable stopper 3, also changes. The molding body 2 according to the invention provides a lumen 5 which permits a rapid volume exchange between the individual partial regions 29, 30 of the inflatable stopper 3. The surface 6 of the molding body 2 according to the invention here offers, if required, a contact surface for the constricted wall region of the inflatable stopper 3. The lumen 5 is thus kept free from these external influences and is completely available for the volume exchange. While the constriction 31 moves along the inflatable stopper 3, the fluid is displaced from the interior 8 of the one partial region 29 of the inflatable stopper 3 via the openings 7, 23, 26, 33 and the lumen 5 into the interior 8 of the other partial region 30 of the inflatable stopper 3.

The invention claimed is:

1. A gastric tube comprising:

an inflatable stopper;

a supply cannula extending in the longitudinal direction for introduction into the oesophagus;

a lumen extending in the longitudinal direction and superposed on the supply cannula in the region of the inflatable stopper, wherein the lumen is connected to the interior of the inflatable stopper, and wherein the lumen permits a rapid volume equalization between various regions of the inflatable stopper; and a separate molding body extending in the longitudinal direction and mounted on the supply cannula entirely within the inflatable stopper, wherein the separate molding body determines the shape of the lumen and has sufficient rigidity to ensure non-collapsible shifting volume, wherein the separate molding body defines a plurality of wall elements, a least one of the wall elements extending in the longitudinal direction in contact with the supply cannula and disposed in the interior of the inflatable stopper.

2. The gastric tube according to claim 1, wherein the molding body has a tubular structure, and wherein the inner contour of the tubular structure approximately corresponds to the outer contour of the supply cannula.

3. The gastric tube according to claim 1, wherein the molding body comprises at least one opening which extends approximately into the longitudinal direction of the molding body over at least 50 to 60% of the overall length of the molding body, and wherein the opening connects the lumen to the interior of the inflatable stopper.

4. The gastric tube according to claim 3, wherein the opening extends approximately over the complete length of the molding body.

5. The gastric tube according to claim 1, wherein the molding body comprises, in the cross-section, a plurality of wall elements extending radially, and wherein each of the wall elements comprises a surface at its extreme ends which extends approximately transversely to the respective wall element.

6. The gastric tube according to claim 5, wherein at least one of the wall elements has an approximately T-shaped profile.

7. The gastric tube according to claim 5, wherein at least one of the wall elements has an approximately L-shaped profile.

8. The gastric tube according to claim 1, wherein the cross-section of the molding body comprises a plurality of wall regions which are supported at the supply cannula of the tube and define, together with it, at least one partial region of the lumen.

9. The gastric tube according to claim 8, wherein each of the wall regions extend approximately like a star into the interior of the molding body.

10. The gastric tube according to claim 1, wherein the lumen is connected, in the region of the axial front side of the molding body, to a supply channel by which the inflatable stopper can be filled with a fluid.

11. The gastric tube according to claim 1, wherein the composition of the molding body is selected from PVC, PUR, mixtures of PVC and PUR, mixtures of PUR and polyamides or silicone, and combinations thereof.

12. The gastric tube according to claim 1, wherein the molding body is manufactured by extruding the molding body.

13. The gastric tube according to claim 1, wherein the molding body engages the supply cannula by an interference fit.

14. The gastric tube according to claim 1, wherein the molding body engages the supply cannula by a frictional engagement.

15. The gastric tube according to claim 1, wherein the molding body engages the supply cannula by adhesion.

16. The gastric tube according to claim 1, wherein the molding body engages the supply cannula by a material connection.

17. The gastric tube according to claim 1, wherein at least a portion of the molding body is treated with a solvent.

18. The gastric tube according to claim 1, wherein an outside diameter of the molding body is between approximately 7 mm to approximately 12 mm.

19. The gastric tube according to claim 1, wherein the outside diameter of the molding body is between approximately 6 mm to approximately 8 mm.

20. The gastric tube according to claim 1, wherein the length of the molding body is between approximately 6 cm to approximately 12 cm.

21. The gastric tube according to claim 1, wherein the length of the molding body is between approximately 6 cm to approximately 9 cm.

22. The gastric tube according to claim 1, wherein the gastric tube has at least one radiopaque marker.

* * * * *